(12) United States Patent
Collins et al.

(10) Patent No.: US 7,674,591 B2
(45) Date of Patent: Mar. 9, 2010

(54) METHODS OF USING ANTIBODIES TO HUMAN IL-13BC FOR INHIBITING IL-13 BINDING

(75) Inventors: Mary Collins, Natick, MA (US); Debra Donaldson, Medford, MA (US); Lori Fitz, Arlington, MA (US); Tamlyn Neben, Acton, MA (US); Matthew Whitters, Hudson, MA (US); Clive Wood, Boston, MA (US)

(73) Assignee: Genetics Institute, LLC, Cambridge, MA (US)

( * ) Notice: Subject to any disclaimer, the term of this patent is extended or adjusted under 35 U.S.C. 154(b) by 136 days.

(21) Appl. No.: 11/362,028

(22) Filed: Feb. 27, 2006

(65) Prior Publication Data
US 2006/0177902 A1 Aug. 10, 2006

Related U.S. Application Data

(60) Division of application No. 09/714,792, filed on Nov. 16, 2000, now Pat. No. 7,078,494, which is a continuation of application No. 08/846,344, filed on Apr. 30, 1997, now Pat. No. 6,268,480, which is a division of application No. 08/609,572, filed on Mar. 1, 1996, now Pat. No. 5,710,023.

(51) Int. Cl.
*G01N 33/567* (2006.01)
*A61K 39/395* (2006.01)
*C07K 14/715* (2006.01)
*C12P 21/06* (2006.01)

(52) U.S. Cl. ............... 435/7.1; 424/145.1; 514/12; 530/351; 536/23.5

(58) Field of Classification Search ............ None
See application file for complete search history.

(56) References Cited

U.S. PATENT DOCUMENTS

| 5,011,912 | A | 4/1991 | Hopp et al. | 530/387 |
| 5,599,905 | A | 2/1997 | Mosley et al. | 530/350 |
| 5,696,234 | A | 12/1997 | Zurawski et al. | 530/351 |
| 2003/0100046 | A1 | 5/2003 | Baumgartner et al. | 435/69.1 |
| 2003/0100047 | A1 | 5/2003 | Baumgartner et al. | 435/69.1 |

FOREIGN PATENT DOCUMENTS

| EP | 0 876 482 | 7/1996 |
| WO | WO 94/04680 | 3/1994 |
| WO | WO/97 15663 | 5/1997 |
| WO | WO 97/20926 | 6/1997 |
| WO | WO 97/33913 | 9/1997 |

OTHER PUBLICATIONS

Wells, 1990, Biochemistry 29:8509-8517.*
Lazar et al, 1988, Mol. Cell. Biol., vol. 8, pp. 1247-1252.*
Arima et al. The Journal of Biological Chemistry, Jul. 2005, vol. 280, No. 26, pp. 24915-24922.*
Lederman et al. 1991, Molecular Immunology, vol. 28, pp. 1171-1181, 1991.*
Li et al. 1980. Proc Natl Aced Sci USA, vol. 77, pp. 3211-3214.*
Husain, et al., "Interleukin-13 Receptor as a Unique Target for Anti-Glioblastoma Therapy", *Int. J. Cancer*, vol. 92 (2001), pp. 168-175.
Barth, "hIL-13 PE38QQR NeoPharm", *Current Opinion in Investigational Drugs*, vol. 2, No. 9 (2001), pp. 1309-1313.
Li, et al., "Targeting glioblastoma multiforme with an IL-13/diphtheria toxin fusion protein in vitro and in vivo in nude mice", *Protein Engineering*, vol. 15, No. 5 (2002), pp. 419-427.
Husain, et al., "Interleukin-13 receptor-directed cytotoxin for malignant glioma therapy: from bench to bedside", *Journal of Neuro-Oncology*, vol. 65 (2003), pp. 37-48.
Mintz, et al., "Molecular targeting with recombinant cytotoxins of interleukin-13 receptor α2-expressing glioma", *Journal of Neuro-Oncology*, vol. 64 (2003), pp. 117-123.
Vita et al., *The Journal of Biological Chemistry*, vol. 270, No. 8 (1995), pp. 3512-3517.
Obiri, et al., *The Journal of Biological Chemistry*, vol. 270, No. 15 (1995), pp. 8797-8804.
Zurawski, et al., *The Journal of Biological Chemistry*, vol. 270, No. 23 (1995), pp. 13869-13878.
McKenzie et al. (1993) "Interleukin-13, a T-cell-derived cytokine that regulates human monocyte and B-cell function" *Proc. Natl. Acad. Sci. U.S.A.* 90:3735-39.
Kawakami, "Cancer Gene Therapy Utilizing Interleukin-13 Receptor α2 Chain", Current Gene Therapy 5:213-223, 2005.
Press release entitled "Neopharm announces additional clinical data for IL-13-PE38 at European Association of Neuro-Oncology (EANO) Congress" http://www.prnewswire.co.uk., 2009.

* cited by examiner

*Primary Examiner*—Manjunath N Rao
*Assistant Examiner*—Fozia M Hamud
(74) *Attorney, Agent, or Firm*—Lando & Anastasi, LLP

(57) ABSTRACT

Polynucleotides encoding the IL-13 receptor and fragments thereof are disclosed. IL-13 receptor proteins, methods for their production, inhibitors of binding of IL-13 and its receptor and methods for their identification are also disclosed.

31 Claims, 1 Drawing Sheet

IL-3 IL-11

IL-4 Mock

Fig. 1

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 1525 base pairs
      (B) TYPE: nucleic acid
      (C) STRANDEDNESS: double
      (D) TOPOLOGY: linear    (ii) MOLECULE TYPE: cDNA    (iii) HYPOTHETICAL: NO    (ix) FEATURE:
      (A) NAME/KEY: CDS
      (B) LOCATION: 256..1404

(xi) SEQUENCE DESCRIPTION: SEQ ID NO: 1:

```
GAATTCGGCA CGAGGGAGAG GAGGAGGGAA AGATAGAAAG AGAGAGAGAA AGATTGCTTG         60

CTACCCCTGA ACAGTGACCT CTCTCAAGAC AGTGCTTTGC TCTTCACGTA TAAGGAAGGA        120

AAACAGTAGA GATTCAATTT AGTGTCTAAT GTGGAAAGGA GGACAAAGAG GTCTTGTGAT        180

AACTGCCTGT GATAATACAT TTCTTGAGAA ACCATATTAT TGAGTAGAGC TTTCAGCACA        240

CTAAATCCTG GAGAA ATG GCT TTT GTG CAT ATC AGA TGC TTG TGT TTC ATT         291
                 Met Ala Phe Val His Ile Arg Cys Leu Cys Phe Ile
                  1               5                  10

CTT CTT TGT ACA ATA ACT GGC TAT TCT TTG GAG ATA AAA GTT AAT CCT          339
Leu Leu Cys Thr Ile Thr Gly Tyr Ser Leu Glu Ile Lys Val Asn Pro
         15                  20                  25

CCT CAG GAT TTT GAA ATA TTG GAT CCT GGA TTA CTT GGT TAT CTC TAT          387
Pro Gln Asp Phe Glu Ile Leu Asp Pro Gly Leu Leu Gly Tyr Leu Tyr
     30                  35                  40

TTG CAA TGG AAA CCT CCT GTG GTT ATA GAA AAA TTT AAG GGC TGT ACA          435
Leu Gln Trp Lys Pro Pro Val Val Ile Glu Lys Phe Lys Gly Cys Thr
 45                  50                  55                  60

CTA GAA TAT GAG TTA AAA TAC CGA AAT GTT GAT AGC GAC AGC TGG AAG          483
Leu Glu Tyr Glu Leu Lys Tyr Arg Asn Val Asp Ser Asp Ser Trp Lys
                 65                  70                  75

ACT ATA ATT ACT AGG AAT CTA ATT TAC AAG GAT GGG TTT GAT CTT AAT          531
Thr Ile Ile Thr Arg Asn Leu Ile Tyr Lys Asp Gly Phe Asp Leu Asn
             80                  85                  90

AAA GGC ATT GAA GGA AAG ATA CGT ACG CAT TTG TCA GAG CAT TGT ACA          579
Lys Gly Ile Glu Gly Lys Ile Arg Thr His Leu Ser Glu His Cys Thr
         95                 100                 105

AAT GGA TCA GAA GTA CAA AGT CCA TGG ATA GAA GCT TCT TAT GGG ATA          627
Asn Gly Ser Glu Val Gln Ser Pro Trp Ile Glu Ala Ser Tyr Gly Ile
    110                 115                 120
```

```
TCA GAT GAA GGA AGT TTG GAA ACT AAA ATT CAG GAC ATG AAG TGT ATA        675
Ser Asp Glu Gly Ser Leu Glu Thr Lys Ile Gln Asp Met Lys Cys Ile
125             130                 135                 140

TAT TAT AAC TGG CAG TAT TTG GTC TGC TCT TGG AAA CCT GGC AAG ACA        723
Tyr Tyr Asn Trp Gln Tyr Leu Val Cys Ser Trp Lys Pro Gly Lys Thr
                145                 150                 155

GTA TAT TCT GAT ACC AAC TAT ACC ATG TTT TTC TGG TAT GAG GGC TTG        771
Val Tyr Ser Asp Thr Asn Tyr Thr Met Phe Phe Trp Tyr Glu Gly Leu
            160                 165                 170

GAT CAT GCC TTA CAG TGT GCT GAT TAC CTC CAG CAT GAT GAA AAA AAT        819
Asp His Ala Leu Gln Cys Ala Asp Tyr Leu Gln His Asp Glu Lys Asn
        175                 180                 185

GTT GGA TGC AAA CTG TCC AAC TTG GAC TCA TCA GAC TAT AAA GAT TTT        867
Val Gly Cys Lys Leu Ser Asn Leu Asp Ser Ser Asp Tyr Lys Asp Phe
    190                 195                 200

TTT ATC TGT GTT AAT GGA TCT TCA AAG TTG GAA CCC ATC AGA TCC AGC        915
Phe Ile Cys Val Asn Gly Ser Ser Lys Leu Glu Pro Ile Arg Ser Ser
205                 210                 215                 220

TAT ACA GTT TTT CAA CTT CAA AAT ATA GTT AAA CCA TTG CCA CCA GAA        963
Tyr Thr Val Phe Gln Leu Gln Asn Ile Val Lys Pro Leu Pro Pro Glu
                225                 230                 235

TTC CTT CAT ATT AGT GTG GAG AAT TCC ATT GAT ATT AGA ATG AAA TGG       1011
Phe Leu His Ile Ser Val Glu Asn Ser Ile Asp Ile Arg Met Lys Trp
            240                 245                 250

AGC ACA CCT GGA GGA CCC ATT CCA CCA AGG TGT TAC ACT TAT GAA ATT       1059
Ser Thr Pro Gly Gly Pro Ile Pro Pro Arg Cys Tyr Thr Tyr Glu Ile
        255                 260                 265

GTG ATC CGA GAA GAC GAT ATT TCC TGG GAG TCT GCC ACA GAC AAA AAC       1107
Val Ile Arg Glu Asp Asp Ile Ser Trp Glu Ser Ala Thr Asp Lys Asn
    270                 275                 280

GAT ATG AAG TTG AAG AGG AGA GCA AAT GAA AGT GAA GAC CTA TGC TTT       1155
Asp Met Lys Leu Lys Arg Arg Ala Asn Glu Ser Glu Asp Leu Cys Phe
285                 290                 295                 300

TTT GTA AGA TGT AAG GTC AAT ATA TAT TGT GCA GAT GAT GGA ATT TGG       1203
Phe Val Arg Cys Lys Val Asn Ile Tyr Cys Ala Asp Asp Gly Ile Trp
                305                 310                 315

AGC GAA TGG AGT GAA GAG GAA TGT TGG GAA GGT TAC ACA GGG CCA GAC       1251
Ser Glu Trp Ser Glu Glu Glu Cys Trp Glu Gly Tyr Thr Gly Pro Asp
            320                 325                 330

TCA AAG ATT ATT TTC ATA GTA CCA GTT TGT CTT TTC TTT ATA TTC CTT       1299
Ser Lys Ile Ile Phe Ile Val Pro Val Cys Leu Phe Phe Ile Phe Leu
        335                 340                 345

TTG TTA CTT CTT TGC CTT ATT GTG GAG AAG GAA GAA CCT GAA CCC ACA       1347
Leu Leu Leu Leu Cys Leu Ile Val Glu Lys Glu Glu Pro Glu Pro Thr
    350                 355                 360

TTG AGC CTC CAT GTG GAT CTG AAC AAA GAA GTG TGT GCT TAT GAA GAT       1395
Leu Ser Leu His Val Asp Leu Asn Lys Glu Val Cys Ala Tyr Glu Asp
365                 370                 375                 380

ACC CTC TGT TAAACCACCA ATTTCTTGAC ATAGAGCCAG CCAGCAGGAG              1444
Thr Leu Cys

TCATATTAAA CTCAATTTCT CTTAAAATTT CGAATACATC TTCTTGAAAA TCCAAAAAAA    1504

AAAAAAAAAA AAAAACTCGA G                                              1525

(2) INFORMATION FOR SEQ ID NO: 2:

(i) SEQUENCE CHARACTERISTICS:
        (A) LENGTH: 383 amino acids
        (B) TYPE: amino acid
        (D) TOPOLOGY: linear
```

(ii) MOLECULE TYPE: protein (xi) SEQUENCE DESCRIPTION: SEQ ID NO: 2:

```
Met Ala Phe Val His Ile Arg Cys Leu Cys Phe Ile Leu Leu Cys Thr
  1               5                  10                  15

Ile Thr Gly Tyr Ser Leu Glu Ile Lys Val Asn Pro Pro Gln Asp Phe
                 20                  25                  30

Glu Ile Leu Asp Pro Gly Leu Leu Gly Tyr Leu Tyr Leu Gln Trp Lys
             35                  40                  45

Pro Pro Val Val Ile Glu Lys Phe Lys Gly Cys Thr Leu Glu Tyr Glu
         50                  55                  60

Leu Lys Tyr Arg Asn Val Asp Ser Asp Ser Trp Lys Thr Ile Ile Thr
 65                  70                  75                  80

Arg Asn Leu Ile Tyr Lys Asp Gly Phe Asp Leu Asn Lys Gly Ile Glu
                 85                  90                  95

Gly Lys Ile Arg Thr His Leu Ser Glu His Cys Thr Asn Gly Ser Glu
            100                 105                 110

Val Gln Ser Pro Trp Ile Glu Ala Ser Tyr Gly Ile Ser Asp Glu Gly
        115                 120                 125

Ser Leu Glu Thr Lys Ile Gln Asp Met Lys Cys Ile Tyr Tyr Asn Trp
130                 135                 140

Gln Tyr Leu Val Cys Ser Trp Lys Pro Gly Lys Thr Val Tyr Ser Asp
145                 150                 155                 160

Thr Asn Tyr Thr Met Phe Phe Trp Tyr Glu Gly Leu Asp His Ala Leu
                165                 170                 175

Gln Cys Ala Asp Tyr Leu Gln His Asp Glu Lys Asn Val Gly Cys Lys
            180                 185                 190

Leu Ser Asn Leu Asp Ser Ser Asp Tyr Lys Asp Phe Phe Ile Cys Val
        195                 200                 205

Asn Gly Ser Ser Lys Leu Glu Pro Ile Arg Ser Ser Tyr Thr Val Phe
210                 215                 220

Gln Leu Gln Asn Ile Val Lys Pro Leu Pro Pro Glu Phe Leu His Ile
225                 230                 235                 240

Ser Val Glu Asn Ser Ile Asp Ile Arg Met Lys Trp Ser Thr Pro Gly
                245                 250                 255

Gly Pro Ile Pro Pro Arg Cys Tyr Thr Tyr Glu Ile Val Ile Arg Glu
            260                 265                 270

Asp Asp Ile Ser Trp Glu Ser Ala Thr Asp Lys Asn Asp Met Lys Leu
        275                 280                 285

Lys Arg Arg Ala Asn Glu Ser Glu Asp Leu Cys Phe Phe Val Arg Cys
290                 295                 300

Lys Val Asn Ile Tyr Cys Ala Asp Asp Gly Ile Trp Ser Glu Trp Ser
305                 310                 315                 320

Glu Glu Glu Cys Trp Gly Tyr Thr Gly Pro Asp Ser Lys Ile Ile
                325                 330                 335

Phe Ile Val Pro Val Cys Leu Phe Phe Ile Phe Leu Leu Leu Leu
            340                 345                 350

Cys Leu Ile Val Glu Lys Glu Pro Glu Pro Thr Leu Ser Leu His
        355                 360                 365

Val Asp Leu Asn Lys Glu Val Cys Ala Tyr Glu Asp Thr Leu Cys
370                 375                 380
```

(2) INFORMATION FOR SEQ ID NO: 3:

(i) SEQUENCE CHARACTERISTICS:
        (A) LENGTH: 1369 base pairs
        (B) TYPE: nucleic acid
        (C) STRANDEDNESS: double
        (D) TOPOLOGY: linear     (ii) MOLECULE TYPE: cDNA     (iii) HYPOTHETICAL: NO     (ix) FEATURE:
        (A) NAME/KEY: CDS
        (B) LOCATION: 103..1245

(xi) SEQUENCE DESCRIPTION: SEQ ID NO: 3:

```
GGATCCGCGC GGATGAAGGC TATTTGAAGT CGCCATAACC TGGTCAGAAG GTGTGCCTGTC        60

GGCGGGGAGA GAGGCAATAT CAAGGTTTTA AATCTCGGAG AA ATG GCT TTC GTT          114
                                               Met Ala Phe Val
                                                1

TGC TTG GCT ATC GGA TGC TTA TAT ACC TTT CTG ATA AGC ACA ACA TTT         162
Cys Leu Ala Ile Gly Cys Leu Tyr Thr Phe Leu Ile Ser Thr Thr Phe
  5              10                  15                  20

GGC TGT ACT TCA TCT TCA GAC ACC GAG ATA AAA GTT AAC CCT CCT CAG         210
Gly Cys Thr Ser Ser Ser Asp Thr Glu Ile Lys Val Asn Pro Pro Gln
             25                  30                  35

GAT TTT GAG ATA GTG GAT CCC GGA TAC TTA GGT TAT CTC TAT TTG CAA         258
Asp Phe Glu Ile Val Asp Pro Gly Tyr Leu Gly Tyr Leu Tyr Leu Gln
                 40                  45                  50

TGG CAA CCC CCA CTG TCT CTG GAT CAT TTT AAG GAA TGC ACA GTG GAA         306
Trp Gln Pro Pro Leu Ser Leu Asp His Phe Lys Glu Cys Thr Val Glu
             55                  60                  65

TAT GAA CTA AAA TAC CGA AAC ATT GGT AGT GAA ACA TGG AAG ACC ATC         354
Tyr Glu Leu Lys Tyr Arg Asn Ile Gly Ser Glu Thr Trp Lys Thr Ile
         70                  75                  80

ATT ACT AAG AAT CTA CAT TAC AAA GAT GGG TTT GAT CTT AAC AAG GGC         402
Ile Thr Lys Asn Leu His Tyr Lys Asp Gly Phe Asp Leu Asn Lys Gly
 85                  90                  95                 100

ATT GAA GCG AAG ATA CAC ACG CTT TTA CCA TGG CAA TGC ACA AAT GGA         450
Ile Glu Ala Lys Ile His Thr Leu Leu Pro Trp Gln Cys Thr Asn Gly
                105                 110                 115

TCA GAA GTT CAA AGT TCC TGG GCA GAA ACT ACT TAT TGG ATA TCA CCA         498
Ser Glu Val Gln Ser Ser Trp Ala Glu Thr Thr Tyr Trp Ile Ser Pro
            120                 125                 130

CAA GGA ATT CCA GAA ACT AAA GTT CAG GAT ATG GAT TGC GTA TAT TAC         546
Gln Gly Ile Pro Glu Thr Lys Val Gln Asp Met Asp Cys Val Tyr Tyr
        135                 140                 145

AAT TGG CAA TAT TTA CTC TGT TCT TGG AAA CCT GGC ATA GGT GTA CTT         594
Asn Trp Gln Tyr Leu Leu Cys Ser Trp Lys Pro Gly Ile Gly Val Leu
150                 155                 160

CTT GAT ACC AAT TAC AAC TTG TTT TAC TGG TAT GAG GGC TTG GAT CAT         642
Leu Asp Thr Asn Tyr Asn Leu Phe Tyr Trp Tyr Glu Gly Leu Asp His
165                 170                 175                 180

GCA TTA CAG TGT GTT GAT TAC ATC AAG GCT GAT GGA CAA AAT ATA GGA         690
Ala Leu Gln Cys Val Asp Tyr Ile Lys Ala Asp Gly Gln Asn Ile Gly
                185                 190                 195

TGC AGA TTT CCC TAT TTG GAG GCA TCA GAC TAT AAA GAT TTC TAT ATT         738
Cys Arg Phe Pro Tyr Leu Glu Ala Ser Asp Tyr Lys Asp Phe Tyr Ile
            200                 205                 210

TGT GTT AAT GGA TCA TCA GAG AAC AAG CCT ATC AGA TCC AGT TAT TTC         786
Cys Val Asn Gly Ser Ser Glu Asn Lys Pro Ile Arg Ser Ser Tyr Phe
        215                 220                 225
```

```
ACT TTT CAG CTT CAA AAT ATA GTT AAA CCT TTG CCG CCA GTC TAT CTT      834
Thr Phe Gln Leu Gln Asn Ile Val Lys Pro Leu Pro Pro Val Tyr Leu
        230                 235                 240

ACT TTT ACT CGG GAG AGT TCA TGT GAA ATT AAG CTG AAA TGG AGC ATA      882
Thr Phe Thr Arg Glu Ser Ser Cys Glu Ile Lys Leu Lys Trp Ser Ile
245                 250                 255                 260

CCT TTG GGA CCT ATT CCA GCA AGG TGT TTT GAT TAT GAA ATT GAG ATC      930
Pro Leu Gly Pro Ile Pro Ala Arg Cys Phe Asp Tyr Glu Ile Glu Ile
                    265                 270                 275

AGA GAA GAT GAT ACT ACC TTG GTG ACT GCT ACA GTT GAA AAT GAA ACA      978
Arg Glu Asp Asp Thr Thr Leu Val Thr Ala Thr Val Glu Asn Glu Thr
                280                 285                 290

TAC ACC TTG AAA ACA ACA AAT GAA ACC CGA CAA TTA TGC TTT GTA GTA     1026
Tyr Thr Leu Lys Thr Thr Asn Glu Thr Arg Gln Leu Cys Phe Val Val
            295                 300                 305

AGA AGC AAA GTG AAT ATT TAT TGC TCA GAT GAC GGA ATT TGG AGT GAG     1074
Arg Ser Lys Val Asn Ile Tyr Cys Ser Asp Asp Gly Ile Trp Ser Glu
        310                 315                 320

TGG AGT GAT AAA CAA TGC TGG GAA GGT GAA GAC CTA TCG AAG AAA ACT     1122
Trp Ser Asp Lys Gln Cys Trp Glu Gly Glu Asp Leu Ser Lys Lys Thr
325                 330                 335                 340

TTG CTA CGT TTC TGG CTA CCA TTT GGT TTC ATC TTA ATA TTA GTT ATA     1170
Leu Leu Arg Phe Trp Leu Pro Phe Gly Phe Ile Leu Ile Leu Val Ile
                    345                 350                 355

TTT GTA ACC GGT CTG CTT TTG CGT AAG CCA AAC ACC TAC CCA AAA ATG     1218
Phe Val Thr Gly Leu Leu Leu Arg Lys Pro Asn Thr Tyr Pro Lys Met
                360                 365                 370

ATT CCA GAA TTT TTC TGT GAT ACA TGA AGACTTTCCA TATCAAGAGA           1265
Ile Pro Glu Phe Phe Cys Asp Thr  *
            375                 380

CATGGTATTG ACTCAACAGT TCCAGTCAT GGCCAAATGT TCAATATGAG TCTCAATAAA    1325

CTGAATTTTT CTTGCGAAAA AAAAAAAAAA AAATCCGCGG ATCC                    1369

(2) INFORMATION FOR SEQ ID NO: 4:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Phe Val Cys Leu Ala Ile Gly Cys Leu Tyr Thr Phe Leu Ile
 1               5                  10                  15

Ser Thr Thr Phe Gly Cys Thr Ser Ser Asp Thr Glu Ile Lys Val
                20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Leu Ser Leu Asp His Phe Lys Glu
        50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110
```

```
Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
        130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
        290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr
370                 375                 380

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 5:

KSRCTCCABK CRCTCCA                                                        17

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 6:
```

-continued

```
ATAGTTAAAC CATTGCCACC                                            20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 7:

CTCCATTCGC TCCAAATTCC                                            20

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 8:

AGTCTATCTT ACTTTTACTC G                                          21

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 9:

CATCTGAGCA ATAAATATTC AC                                         22
```

METHODS OF USING ANTIBODIES TO HUMAN IL-13BC FOR INHIBITING IL-13 BINDING

This application is a division of application Ser. No. 09/714,792 filed Nov. 16, 2000 (now U.S. Pat. No. 7,078,494), which in turn is a continuation of application Ser. No. 08/846,344 filed Apr. 30, 1997 (now U.S. Pat. No. 6,268,480), which in turn is a division of application Ser. No. 08/609,572 filed Mar. 1, 1996 (now U.S. Pat. No. 5,710,023).

FIELD OF THE INVENTION

The present invention relates to mammalian cytokine receptor proteins with affinity for IL-13 (including without limitation human and murine receptor proteins), fragments thereof and recombinant polynucleotides and cells useful for expressing such proteins.

BACKGROUND OF THE INVENTION

A variety of regulatory molecules, known as cytokines, have been identified including interleukin-13 (IL-13). Various protein forms of IL-13 and DNA encoding various forms of IL-13 activity are described in McKenzie et al., Proc. Natl. Acad. Sci. USA 90:3735 (1995); Minty et al., Nature 362:248 (1993); and Aversa et al., WO94/04680. Thus, the term "IL-13" includes proteins having the sequence and/or biological activity described in these documents, whether produced by recombinant genetic engineering techniques; purified from cell sources producing the factor naturally or upon induction with other factors; or synthesized by chemical techniques; or a combination of the foregoing.

IL-13 is a cytokine that has been implicated in production of several biological activities including: induction of IgG4 and IgE switching, including in human immature B cells (Punnonen et al., J. Immunol. 152:1094 (1994)); induction of germ line IgE heavy chain (E) transcription and CD23 expression in normal human B cells (Punnonen et al., Proc. Natl. Acad. Sci. USA 90:3730 (1993)); and induction of B cell proliferation in the presence of CD40L or anti-CD40 mAb (Cocks et al., Int. Immunol. 5:657 (1993)). Although many activities of IL-13 are similar to those of IL-4, in contrast to IL-4, IL-13 does not have growth promoting effects on activated T cells or T cell clones (Zurawski et al., EMBO J. 12:2663 (1993)).

Like most cytokines, IL-13 exhibits certain biological activities by interacting with an IL-13 receptor ("IL-13R") on the surface of target cells. IL-13R and the IL-4 receptor ("IL-4R") sharing a common component, which is required for receptor activation; however, IL-13 does not bind to cells transfected with the 130 kD IL-4R (Zurawski et al., supra). Thus, the IL-13R must contain at least one other ligand binding chain. Cytokine receptors are commonly composed or two or three chains. The cloning of one ligand binding chain for IL-13 has been recently reported (Hilton et al., Proc. Natl. Acad. Sci. 93:497-501).

It would be desirable to identify and clone the sequence for any other IL-13 binding chain of IL-13R so that IL-13R proteins can be produced for various reasons, including production of therapeutics and screening for inhibitors of IL-13 binding to the receptor and receptor signaling.

SUMMARY OF THE INVENTION

In accordance with the present invention, polynucleotides encoding the IL-13 binding chains of the interleukin-13 receptor are disclosed, including without limitation those from the murine and human receptors. In certain embodiments, the invention provides an isolated polynucleotide comprising a nucleotide sequence selected from the group consisting of:

(a) the nucleotide sequence of SEQ ID NO:1 from nucleotide 256 to nucleotide 1404;

(b) the nucleotide sequence of SEQ ID NO:3 from nucleotide 103 to nucleotide 1242;

(c) a nucleotide sequence varying from the sequence of the nucleotide sequence specified in (a) or (b) as a result of degeneracy of the genetic code;

(d) a nucleotide sequence capable of hybridizing under stringent conditions to the nucleotide specified in (a) or (b);

(e) a nucleotide sequence encoding a species homologue of the sequence specified in (a) or (b); and (f) an allelic variant of the nucleotide sequence specified in (a) or (b).

Preferably, the nucleotide sequence encodes a protein having a biological activity of the human IL-13 receptor. The nucleotide sequence may be operably linked to an expression control sequence. In preferred embodiments, the polynucleotide comprises the nucleotide sequence of SEQ ID NO:1 from nucleotide 256 to nucleotide 1404; the nucleotide sequence of SEQ ID NO:1 from nucleotide 319 to nucleotide 1257; the nucleotide sequence of SEQ ID NO:1 from nucleotide 1324 to nucleotide 1404; the nucleotide sequence of SEQ ID NO:3 from nucleotide 103 to nucleotide 1242; the nucleotide sequence of SEQ ID NO:3 from nucleotide 178 to nucleotide 1125; or the nucleotide sequence of SEQ ID NO:3 from nucleotide 1189 to nucleotide 1242.

The invention also provides isolated polynucleotides comprising a nucleotide sequence encoding a peptide or protein comprising an amino acid sequence selected from the group consisting of:

(a) the amino acid sequence of SEQ ID NO:2;

(b) the amino acid sequence of SEQ ID NO:2 from amino acids 22 to 334;

(c) the amino acid sequence of SEQ ID NO:2 from amino acids 357 to 383;

(d) the amino acid sequence of SEQ ID NO:4;

(e) the amino acid sequence of SEQ ID NO:4 from amino acids 26 to 341;

(f) the amino acid sequence of SEQ ID NO:4 from amino acids 363 to 380; and (g) fragments of (a)-(f) having a biological activity of the IL-13 receptor binding chain. Other preferred embodiments encode the amino acid sequence of SEQ ID NO:2 from amino acids 1 or 331 and the amino acid sequence of SEQ ID NO:2 from amino acids 26 to 331.

Host cells, preferably mammalian cells, transformed with the polynucleotides are also provided.

In other embodiments, the invention provides a process for producing a IL-13bc protein. The process comprises:

(a) growing a culture of the host cell of the present invention in a suitable culture medium; and (b) purifying the human IL-13bc protein from the culture.

Proteins produced according to these methods are also provided.

The present invention also provides for an isolated IL-13bc protein comprising an amino acid sequence selected from the group consisting of:

(a) the amino acid sequence of SEQ ID NO:2;

(b) the amino acid sequence of SEQ ID NO:2 from amino acids 22 to 334;

(c) the amino acid sequence of SEQ ID NO:2 from amino acids 357 to 383;
(d) the amino acid sequence of SEQ ID NO:4;
(e) the amino acid sequence of SEQ ID NO:4 from amino acids 26 to 341;
(f) the amino acid sequence of SEQ ID NO:4 from amino acids 363 to 380; and
(g) fragments of (a)-(f) having a biological activity of the IL-13 receptor binding chain Preferably the protein comprises the amino acid sequence of SEQ ID NO:2; the sequence from amino acid 22 to 334 of SEQ ID NO:2; the sequence of SEQ ID NO:4; or the sequence from amino acid 26 to 341 of SEQ ID NO:4. In other preferred embodiments, the specified amino acid sequence is part of a fusion protein (with an additional amino acid sequence not derived from IL-13bc). Preferred fusion proteins comprise an antibody fragment, such as an Fc fragment. Particularly preferred embodiments comprise the amino acid sequence of SEQ ID NO:2 from amino acids 1 to 331 and the amino acid sequence of SEQ ID NO:2 from amino acids 26 to 331.

Pharmaceutical compositions comprising a protein of the present invention and a pharmaceutically acceptable carrier are also provided.

The present invention further provides for compositions comprising an antibody which specifically reacts with a protein of the present invention.

Methods of identifying an inhibitor of IL-13 binding to the IL-13bc or IL-13 receptor are also provided. These methods comprise:
(a) combining an IL-13bc protein or a fragment thereof with IL-13 or a fragment thereof, said combination forming a first binding mixture;
(b) measuring the amount of binding between the protein and the IL-13 or fragment in the first binding mixture;
(c) combining a compound with the protein and the IL-13 or fragment to form a second binding mixture;
(d) measuring the amount of binding in the second binding mixture; and
(e) comparing the amount of binding in the first binding mixture with the amount of binding in the second binding mixture;

wherein the compound is capable of inhibiting IL-13 binding to the IL-13bc protein or IL-13 receptor when a decrease in the amount of binding of the second binding mixture occurs. Inhibitors of IL-13 R identified by these methods and pharmaceutical compositions containing them are also provided.

Methods of inhibiting binding of IL-13 to the IL-13bc proteins or IL-13 receptor in a mammalian subject are also disclosed which comprise administering a therapeutically effective amount of a composition containing an IL-13bc protein, an IL-13bc or IL-13R inhibitor or an antibody to an IL-13bc protein.

Methods are also provided for potentiating IL-13 activity, which comprise combining a protein having IL-13 activity an isolated IL-13bc protein comprising an amino acid sequence selected from the group consisting of:
(a) the amino acid sequence of SEQ ID NO:2;
(b) the amino acid sequence of SEQ ID NO:2 from amino acids 22 to 334;
(c) the amino acid sequence of SEQ ID NO:2 from amino acids 357 to 383;
(d) the amino acid sequence of SEQ ID NO:4;
(e) the amino acid sequence of SEQ ID NO:4 from amino acids 26 to 341;
(f) the amino acid sequence of SEQ ID NO:4 from amino acids 363 to 380; and
(g) fragments of (a)-(f) having a biological activity of the IL-13 receptor binding chain; and contacting such combination with a cell expressing at least one chain of IL-13R other than IL-13bc. Preferably, the contacting step is performed by administering a therapeutically effective amount of such combination to a mammalian subject.

BRIEF DESCRIPTION OF THE FIGURE

The FIGURE presents photographs of IL-13, IL-4, IL-11 and mock transfected COS cells after exposure to IL-13bc-Fc as described in Example 4 below.

DETAILED DESCRIPTION OF PREFERRED EMBODIMENTS

The inventors of the present application have for the first time identified and provided polynucleotides encoding the IL-13 binding chain of IL-13R (hereinafter "IL-13bc"), including without limitation polynucleotides encoding murine and human IL-13bc.

SEQ ID NO: 1 provides the nucleotide sequence of a cDNA encoding the murine IL-13bc. SEQ ID NO:2 provides the predicted amino acid sequence of the receptor chain, including a putative signal sequence from amino acids 1-21. The mature murine IL-13bc is believed to have the sequence of amino acids 22-383 of SEQ ID NO:2. The mature murine receptor chain has at least three distinct domains: an extracellular domain (comprising approximately amino acids 22-334 of SEQ ID NO:2), a transmembrane domain (comprising approximately amino acids 335-356 of SEQ ID NO:2) and an intracellular domain (comprising approximately amino acids 357-383 of SEQ ID NO:2).

SEQ ID NO:3 provides the nucleotide sequence of a cDNA encoding the human IL-13bc. SEQ ID NO:4 provides the predicted amino acid sequence of the receptor chain, including a putative signal sequence from amino acids 1-25. The mature human IL-13bc is believed to have the sequence of amino acids 26-380 of SEQ ID NO:4. The mature human receptor chain has at least three distinct domains: an extracellular domain (comprising approximately amino acids 26-341 or SEQ ID NO:4), a transmembrane domain (comprising approximately amino acids 342-362 of SEQ ID NO:4) and an intracellular domain (comprising approximately amino acids 363-380 of SEQ ID NO:4).

The first 81 amino acids of the human IL-13bc sequence are identical to the translated sequence of an expressed sequence tag (EST) identified as "yg99f10.r1 *Homo sapiens* cDNA clone 41648 5'" and assigned database accession number R52795.gb_est2. There are no homologies or sequence motifs in this EST sequence which would lead those skilled in the art to identify the encoded protein as a cytokine receptor.

Soluble forms of IL-13bc protein can also be produced. Such soluble forms include without limitation proteins comprising amino acids 1-334 or 22-334 of SEQ ID NO:2 or amino acids 1-341 or 26-341 of SEQ ID NO:4. The soluble forms of the IL-13bc are further characterized by being soluble in aqueous solution, preferably at room temperature. IL-13bc proteins comprising only the intracellular domain or a portion thereof may also be produced. Any forms of IL-13bc of less than full length are encompassed within the present invention and are referred to herein collectively with full length and mature forms as "IL-13bc" or "IL-13bc proteins." IL-13bc proteins of less than full length may be produced by expressing a corresponding fragment of the polynucleotide encoding the full-length IL-13bc protein (SEQ ID NO:1 or SEQ ID NO:3). These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

For the purposes of the present invention, a protein has "a biological activity of the IL-13 receptor binding chain" if it possesses one or more of the following characteristics: (1) the ability to bind IL-13 or a fragment thereof (preferably a biologically active fragment thereof); and/or (2) the ability to interact with the second non-IL-13-binding chain of IL-13R to produce a signal characteristic of the binding of IL-13 to IL-13R. Preferably, the biological activity possessed by the protein is the ability to bind IL-13 or a fragment thereof, more preferably with a $K_D$ of about 0.1 to about 100 nM. Methods for determining whether a particular protein or peptide has such activity include without limitation the methods described in the examples provided herein.

IL-13bc or active fragments thereof (IL-13bc proteins) may be fused to carrier molecules such as immunoglobulins. For example, soluble forms of the IL-13bc may be fused through "linker" sequences to the Fc portion of an immunoglobulin. Other fusions proteins, such as those with GST, Lex-A or MBP, may also be used.

The invention also encompasses allelic variants of the nucleotide sequences as set forth in SEQ ID NO:1 or SEQ ID NO:3, that is, naturally-occurring alternative forms of the isolated polynucleotide of SEQ ID NO:1 or SEQ ID NO:3 which also encode IL-13bc proteins, preferably those proteins having a biological activity of IL-13bc. Also included in the invention are isolated polynucleotides which hybridize to the nucleotide sequence set forth in SEQ ID NO:1 or SEQ ID NO:3 under highly stringent conditions (for example, 0.1× SSC at 65° C.). Isolated polynucleotides which encode IL-13bc proteins but which differ from the nucleotide sequence set forth in SEQ ID NO:1 or SEQ ID NO:3 by virtue of the degeneracy of the genetic code are also encompassed by the present invention. Variations in the nucleotide sequence as set forth in SEQ ID NO:1 or SEQ ID NO:3 which are caused by point mutations or by induced modifications are also included in the invention.

The present invention also provides polynucleotides encoding homologues of the murine and human IL-13bc from other animal species, particularly other mammalian species. Species homologues can be identified and isolated by making probes or primers from the murine or human sequences disclosed herein and screening a library from an appropriate species, such as for example libraries constructed from PBMCs, thymus or testis of the relevant species.

The isolated polynucleotides of the invention may be operably linked to an expression control sequence such as the pMT2 or pED expression vectors disclosed in Kaufman et al., Nucleic Acids Res. 19, 4485-4490 (1991), in order to produce the IL-13bc protein recombinantly. Many suitable expression control sequences are known in the art. General methods of expressing recombinant proteins are also known and are exemplified in R. Kaufman, Methods in Enzymology 185, 537-566 (1990). As defined herein "operably linked" means enzymatically or chemically ligated to form a covalent bond between the isolated polynucleotide of the invention and the expression control sequence, in such a way that the IL-13bc protein is expressed by a host cell which has been transformed (transfected) with the ligated polynucleotide/expression control sequence.

A number of types of cells may act as suitable host cells for expression of the IL-13bc protein. Any cell type capable of expressing functional IL-13bc protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, M1x or C2C12 cells.

The IL-13bc protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. Soluble forms of the IL-13bc protein may also be produced in insect cells using appropriate isolated polynucleotides as described above.

Alternatively, the IL-13bc protein may be produced in lower eukaryotes such as yeast or in prokaryotes such as bacteria. Suitable yeast strains include *Saccharomyces cerevisiae*, *Schizosaccharomyces pombe*, *Kluyveromyces* strains, *Candida*, or any yeast strain capable of expressing heterologous proteins. Suitable bacterial strains include *Escherichia coli, Bacillus subtilis, Salmonella typhimurium*, or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, *Meth. Enzym.*, 185:187-195 (1990). EP 0433225 and copending application U.S. Ser. No. 08/163,877 describe other appropriate methods.

The IL-13bc protein of the invention may also be expressed as a product of transgenic animals, e.g., as a component of the milk of transgenic cows, goats, pigs, or sheep which are characterized by somatic or germ cells containing a polynucleotide sequence encoding the IL-13bc protein.

The IL-13bc protein of the invention may be prepared by growing a culture transformed host cells under culture conditions necessary to express the desired protein. The resulting expressed protein may then be purified from the culture medium or cell extracts. Soluble forms of the IL-13bc protein of the invention can be purified from conditioned media. Membrane-bound forms of IL-13bc protein of the invention can be purified by preparing a total membrane fraction from the expressing cell and extracting the membranes with a non-ionic detergent such as Triton X-100.

The IL-13bc protein can be purified using methods known to those skilled in the art. For example, the IL-13bc protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the IL-13bc protein from culture supernatant may also include one or more column steps over such affinity resins as concanavalin A-agarose, Heparin-Toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the IL-13bc protein. Affinity columns including IL-13 or fragments thereof or including antibodies to the IL-13bc protein can also be used in purification in accordance with known methods. Some or all of the foregoing purification steps, in various combinations or with other known methods, can also be employed to provide a substantially purified isolated recombinant protein. Preferably, the isolated IL-13bc protein is purified so that it is substantially free of other mammalian proteins.

IL-13bc proteins of the invention may also be used to screen for agents which are capable of binding to IL-13bc or IL-13R or which interfere with the binding of IL-13 to the IL-13 or IL-13bc (either the extracellular or intracellular domains) and thus may act as inhibitors of normal binding and cytokine action ("IL-13R inhibitors"). Binding assays using a desired binding protein, immobilized or not, are well known in the art and may be used for this purpose using the IL-13bc protein of the invention. Purified cell based or protein based (cell free) screening assays may be used to identify such agents. For example, IL-13bc protein may be immobilized in purified form on a carrier and binding to purified IL-13bc protein may be measured in the presence and in the absence of potential inhibiting agents. A suitable binding assay may alternatively employ a soluble form of IL-13bc of the invention. Another example of a system in which inhibitors may be screened is described in Example 2 below.

In such a screening assay, a first binding mixture is formed by combining IL-13 or a fragment thereof and IL-13bc protein, and the amount of binding in the first binding mixture ($B_0$) is measured. A second binding mixture is also formed by combining IL-13 or a fragment thereof, IL-13bc protein, and the compound or agent to be screened, and the amount of binding in the second binding mixture (B) is measured. The amounts of binding in the first and second binding mixtures are compared, for example, by performing a calculation of the ratio $B/B_0$. A compound or agent is considered to be capable of inhibiting binding if a decrease in binding in the second binding mixture as compared to the first binding mixture is observed. Optionally, the second chain of IL-13R can be added to one or both of the binding mixtures. The formulation and optimization of binding mixtures is within the level of skill in the art, such binding mixtures may also contain buffers and salts necessary to enhance or to optimize binding, and additional control assays may be included in the screening assay of the invention.

Compounds found to reduce the binding activity of IL-13bc protein to IL-13 or its fragment to any degree, preferably by at least about 10%, more preferably greater than about 50% or more, may thus be identified and then secondarily screened in other binding assays and in vivo assays. By these means compounds having inhibitory activity for IL-13bc binding which may be suitable as therapeutic agents may be identified.

IL-13bc proteins, and polynucleotides encoding them, may also be used as diagnostic agents for detecting the expression or presence of IL-13bc, IL-13R, IL-13 or cells expressing IL-13bc, IL-13R or IL-13. The proteins or polynucleotides may be employed for such purpose in standard procedures for diagnostics assays using these types of materials. Suitable methods are well known to those skilled in the art.

IL-13bc acts as a mediator of the known biological activities of IL-13. As a result, IL-13bc protein (particularly, soluble IL-13bc proteins) and IL-13R inhibitors may be useful in treatment or modulation of various medical conditions in which IL-13 is implicated or which are effected by the activity (or lack thereof) of IL-13 (collectively "IL-13-related conditions"). IL-13-related conditions include without limitation Ig-mediated conditions and diseases, particularly IgE-mediated conditions (including without limitation allergic conditions, asthma, immune complex disease (such as, for example, lupus, nephrotic syndrome, nephritis, glomerulonephritis, thyroiditis and Grave's disease)); immune deficiencies, specifically deficiencies in hematopoietic progenitor cells, or disorders relating thereto; cancer and other disease. Such pathological states may result from disease, exposure to radiation or drugs, and include, for example, leukopenia, bacterial and viral infections, anemia, B cell or T cell deficiencies such as immune cell or hematopoietic cell deficiency following a bone marrow transplantation. Since IL-12 inhibits macrophage activation, IL-13bc proteins may also be useful to enhance macrophage activation (i.e., in vaccination, treatment of mycobacterial or intracellular organisms, or parasitic infections).

IL-13bc proteins may also be used to potentiate the effects of IL-13 in vitro and in vivo. For example, an IL-13bc protein can be combined with a protein having IL-13 activity (preferably IL-13) and the resulting combination can be contacted with a cell expressing at least one chain of IL-13R other than IL-13bc (preferably all chains of IL-13R other than IL-13bc). Preferably, the contacting step is performed by administering a therapeutically effective amount of such combination to a mammalian subject in vivo. The pre-established association of the IL-13 protein with the IL-13bc protein will aid in formation of the complete IL-13/IL-13R complex necessary for proper signaling. See for example the methods described by Economides et al., Science 270:1351 (1995).

IL-13bc protein and IL-13R inhibitors, purified from cells or recombinantly produced, may be used as a pharmaceutical composition when combined with a pharmaceutically acceptable carrier. Such a composition may contain, in addition to IL-13bc or inhibitor and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-14, IL-15, G-CSF, stem cell factor, and erythropoietin. The pharmaceutical composition may also include anti-cytokine antibodies. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with isolated IL-13bc protein or IL-13bc inhibitor, or to minimize side effects caused by the isolated IL-13bc or IL-13bc inhibitor. Conversely, isolated IL-13bc or IL-13bc inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated IL-13bc protein or IL-13bc inhibitor is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,827,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated IL-13bc protein or IL-13bc inhibitor is administered to a mammal. Isolated IL-13bc protein or IL-13bc inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, IL-13bc protein or IL-13bc inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering IL-13bc protein or IL-13bc inhibitor in combination with cytokine(s), lymphokine(s), other hematopoietic factor(s), thrombolytic or anti-thrombotic factors.

Administration of IL-13bc protein or IL-13bc inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of IL-13bc protein or IL-13bc inhibitor is administered orally, IL-13bc protein or IL-13bc inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% IL-13bc protein or IL-13bc inhibitor, and preferably from about 25 to 90% IL-13bc protein or IL-13bc inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of IL-13bc protein or IL-13bc inhibitor, and preferably from about 1 to 50% IL-13bc protein or IL-13bc inhibitor.

When a therapeutically effective amount of IL-13bc protein or IL-13bc inhibitor is administered by intravenous, cutaneous or subcutaneous injection, IL-13bc protein or IL-13bc inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to IL-13bc protein or IL-13bc inhibitor an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of IL-13bc protein or IL-13bc inhibitor in the pharmaceutical composition of the present invention will depend upon the nature and severity of the condition being treated, and on the nature of prior treatments which the patient has undergone. Ultimately, the attending physician will decide the amount of IL-13bc protein or IL-13bc inhibitor with which to treat each individual patient. Initially, the attending physician will administer low doses of IL-13bc protein or IL-13bc inhibitor and observe the patient's response. Larger doses of IL-13bc protein or IL-13bc inhibitor may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of IL-13bc protein or IL-13bc inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the IL-13bc protein or IL-13bc inhibitor will be in the range of 12 to 24 hours of continuous intravenous administration. Ultimately the attending physician will decide on the appropriate duration of intravenous therapy using the pharmaceutical composition of the present invention.

IL-13bc proteins of the invention may also be used to immunize animals to obtain polyclonal and monoclonal antibodies which specifically react with the IL-13bc protein and which may inhibit binding of IL-13 or fragments thereof to the receptor. Such antibodies may be obtained using the entire IL-13bc as an immunogen, or by using fragments of IL-13bc, such as the soluble mature IL-13bc. Smaller fragments of the IL-13bc may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149-2154 (1963); J. L. Krstenansky, et al., FEBS Lett. 211, 10 (1987).

Neutralizing or non-neutralizing antibodies (preferably monoclonal antibodies) binding to IL-13bc protein may also be useful therapeutics for certain tumors and also in the treatment of conditions described above. These neutralizing monoclonal antibodies may be capable of blocking IL-13 binding to the IL-13bc.

EXAMPLE 1

Isolation of IL-13bc cDNAs

Isolation of the Murine IL-13 Receptor Chain.

5 ug of polyA+ RNA was prepared from the thymuses of 6-8 week old C3H/HeJ mice. Double stranded, hemimethylated cDNA was prepared using Stratagene's cDNA synthesis kit according to manufacturer's instructions. Briefly, the first strand was primed with an oligodT-Xho primer, and after second strand synthesis, EcoRI adapters were added, and the cDNA was digested with XhoI, and purified. The cDNA was ligated to the XhoI-EcoRI sites of the Zap Express (Stratagene) lambda vector, and packaged, using Gigapak II Gold packaging extracts (Stratagene) according to the manufacturer's instructions. A library of $1.5 \times 10^6$ resulting recombinant phage was amplified following manufacturer's instructions. This library was screened with a degenerate 17mer oligonucleotide probe of the sequence KSRCTCCABK CRCTCCA (SEQ ID NO:5) (K=G+T; S=C+G; R=A+G; B=C+G+T) using standard TMAC hybridization conditions as described (Current Protocols in Molecular Biology, Ausubel, et al., editors., John Wiley and Sons, 1995, section 6.4.3). Clone A25 was identified because it hybridized to the 17mer probe, but not to probes derived from known hematopoietin receptors. This clone was isolated in plasmid form from the ZapExpress vector as per manufacturer's instruction, and the DNA sequence was determined. The DNA sequence encoded a novel member of the hematopoietin receptor family.

Clone A25 containing the polynucleotide having the sequence of SEQ ID NO: 1 was deposited with ATCC as pA25pBKCMV at accession number 69997 on Feb. 22, 1996.

Isolation of the Human IL-13 Receptor Chain.

A partial fragment of the human homolog of the murine receptor was isolated by PCR using oligonucleotides derived from the murine sequence. cDNA was prepared from human testis polyA+ RNA that was obtained from Clontech. A DNA fragment of 274 base pairs was amplified from this cDNA by PCR with the following oligonucleotides: ATAGTTAAAC-CATTGCCACC (SEQ ID NO:6) and CTCCATTCGCTC-CAAATTCC (SEQ ID NO:7) using AmpliTaq polymerase (Promega) in 1×Taq buffer containing 1.5 mM MgCl2 for 30 cycles of incubation (94° C.×1 minute, 42° C. for 1 minute, and 72° C. for 1 minute). The DNA sequence of this fragment was determined, and two oligonucleotides were prepared from an internal portion of this fragment with the following sequence: AGTCTATCTTACTTTTACTCG (SEQ ID NO: 8) and CATCTGAGCAATAAATATTCAC (SEQ ID NO: 9). These oligonucleotides were used as probes to screen a human testis cDNA library purchased from CLONTECH (cat #HL1161). Filters were hybridized at 52° C. using standard 5×SSC hybridization conditions and washed in 2×SSC at 52° C. Twenty two clones were isolated that hybridized to both oligonucleotides in a screen of 400,000 clones. DNA sequence was determined from four of the cDNA clones, and all encoded the same novel hematopoietin receptor. The predicted DNA sequence of the full length human receptor chain is shown as SEQ ID NO:3.

The human clone was deposited with ATCC as phA25#11pDR2 at accession number 69998 on Feb. 22, 1996.

EXAMPLE 2

Expression of Soluble IL-13bc Protein and Assay of Activity

Production and Purification of Soluble IL-13bc-Ig.

DNA encoding amino acids 1-331 of the extracellular domain of murine IL-13bc was fused to a spacer sequence encoding gly-ser-gly by PCR and ligated in frame with sequences encoding the hinge CH2 CH3 regions of human IgG1 of the COS-1 expression vector pED.Fc. IL-13bc-Ig was produced from DEAE-dextran transfected COS-1 cells and purified via protein A sepharose chromatography (Pharmacia).

B9 Proliferation Assay

Stimulation of proliferation of B9 cells (Aarden et al. Eur. J. Immunol. 1987. 17:1411-1416) in response to IL-13 or IL-4 was measured by 3H-thymidine incorporation into DNA. Cells (5×103/well) were seeded into 96 well plates with media containing growth factors at varying concentrations in the presence or absence of IL-13bc-Ig at 1 ug/ml. After incubation for 3 days 1 uCi/well of 3H-thymidine was added and the cells incubated for an additional 4 hrs. Incorporated radioactivity was determined using a LKB 1205 Plate reader.

The B9 cell line proliferated in response to IL-13, IL-4 or IL-6. Only responses to IL-13 were inhibited by the soluble IL-13bc-Ig, indicating that this receptor binds IL-13 specifically, but not IL-4 or IL-6. The tables show cpm. Two separate experiments are shown.

| cytokine dilution | IL-13 (3 ng/ml) | IL-13 plus A25-Fc (1 ug/ml) | IL-4 (20 ng/ml) | IL-4 plus A25-Fc (1 ug/ml) | Cos IL-6 (1/10,000) |
|---|---|---|---|---|---|
| 1 | 37734 | 1943 | 6443 | 6945 | 37887 |
| 1/3 | 30398 | 1571 | 2680 | 2442 | 36500 |
| 1/10 | 16101 | 1461 | 1767 | 1771 | 33335 |
| 1/30 | 2148 | 1567 | 1619 | 1783 | 27271 |
| 1/100 | 1574 | 1419 | 1522 | 1576 | 18831 |
| 1/300 | 1512 | 1531 | 1373 | 1577 | 7768 |
| 1/1000 | 1316 | 1392 | 1190 | 1474 | 2760 |
| 1/3000 | 1834 | 1994 | 1482 | 1819 | 1672 |

| cytokine dilution | IL-13 (3 ng/ml) | IL-13 plus A25-Fc (5 ug/ml) | IL-4 (20 ng/ml) | IL-4 plus A25-Fc (5 ug/ml) | Cos IL-6 (1/10,000) | Cos IL-6 plus A25-Fc (5 ug/ml) |
|---|---|---|---|---|---|---|
| 1 | 6413 | 295 | 1216 | 1158 | 6969 | 7703 |
| 1/3 | 5432 | 281 | 518 | 656 | 7827 | 8804 |
| 1/10 | 2051 | 281 | 489 | 520 | 8345 | 10027 |

-continued

| cytokine dilution | IL-13 (3 ng/ml) | IL-13 plus A25-Fc (5 ug/ml) | IL-4 (20 ng/ml) | IL-4 plus A25-Fc (5 ug/ml) | Cos IL-6 (1/10,000) | Cos IL-6 plus A25-Fc (5 ug/ml) |
|---|---|---|---|---|---|---|
| 1/30 | 506 | 319 | 279 | 476 | 8680 | 9114 |
| 1/100 | 430 | 372 | 288 | 423 | 7426 | 10364 |
| 1/300 | 330 | 287 | 323 | 420 | 5531 | 6254 |
| 1/1000 | 326 | 389 | 348 | nt | 2524 | nt |
| no cytokine | 339 | 279 | 404 | 394 | 326 | 279 |

EXAMPLE 3

Direct Binding of Soluble IL-13bc to IL-13 Measured by Surface Plasmon Resonance (Biacore Analysis)

A Biacore biosensor was used to measure directly the specific binding of IL-13 to purified IL-13bc-Ig (Pharmacia, Johnsson et al., 1991). Approximately 10,000 to 17,000 resonance units (RU) of purified IL-13bc-Ig, human IgG1 or irrelevant receptor were each covalently immobilized to different flow cells on the sensor chip as recommended by the manufacturer. (RU's are a reflection of the mass of protein bound to the sensor chip surface.) Purified IL-13 was injected across the flow cells at 5 ul/min for 10 mins in the presence or absence of excess purified IL-13bc-Ig. Binding was quantified as the difference in RU before and after sample injection. Specific IL-13 binding of 481.9 RU was observed only for immobilized IL-13bc-Ig whereas coinjection of IL-13 plus IL-13bc-Ig resulted in no binding to the immobilized IL-13bc-Ig (4 RU). No IL-13 binding was observed for either immobilized IgG or IL-11R-Ig (5.4 and 3.7 RU respectively).

| Sample | IL-13BC-Ig (10,383 RU) | IgG control (13,399 RU) | IL-11R-Ig (17,182 RU) |
|---|---|---|---|
| 100 ng/ml human IL-13 | 481.9 RU bound | 5.4 RU bound | 3.7 RU bound |
| 100 ng/ml human IL-13 + soluble IL-13BC-Ig | 4.0 RU bound | not tested | not tested |

EXAMPLE 4

Binding of IL-13 Expressed in COS Cells to Labeled IL-13BC-Ig Fusion Protein

COS In Situ Detection of IL-13 with IL-13bc-Fc

Expression vectors for IL-13, IL-4, IL-11 or empty vector were transfected into COS-1 cells in duplicated plates via the DEAE-dextran method. Two days after transfection cells were washed twice in phosphate buffered saline (PBS) and fixed in the culture dish for 10' at 4° C. with methanol. Following fixation cells were washed twice with PBS then rinsed once with binding buffer (PBS, 1% (w/v) bovine serum albumin,) 0.1% (w/v) sodium azide) and incubated for two hours at 4° C. in binding buffer with IL-13bc-Fc at 1.0 ug/ml or with relevant anti-cytokine antisera. Cells were washed twice with PBS and incubated at 4° C. with shaking in alkaline phosphatase labeled Rabbit F(ab)2' anti-human IgG diluted 1:500 in binding buffer (for Fc fusion detection) or Rabbit F(ab)2' anti-rat IgG (for anti-cytokine detection). Cells were again washed twice in PBS. Alkaline phosphatase activity was visualized using nitro blue tetrazolium and 5-bromo-4-chloro-3-indolyl-phosphate.

Figure 1:
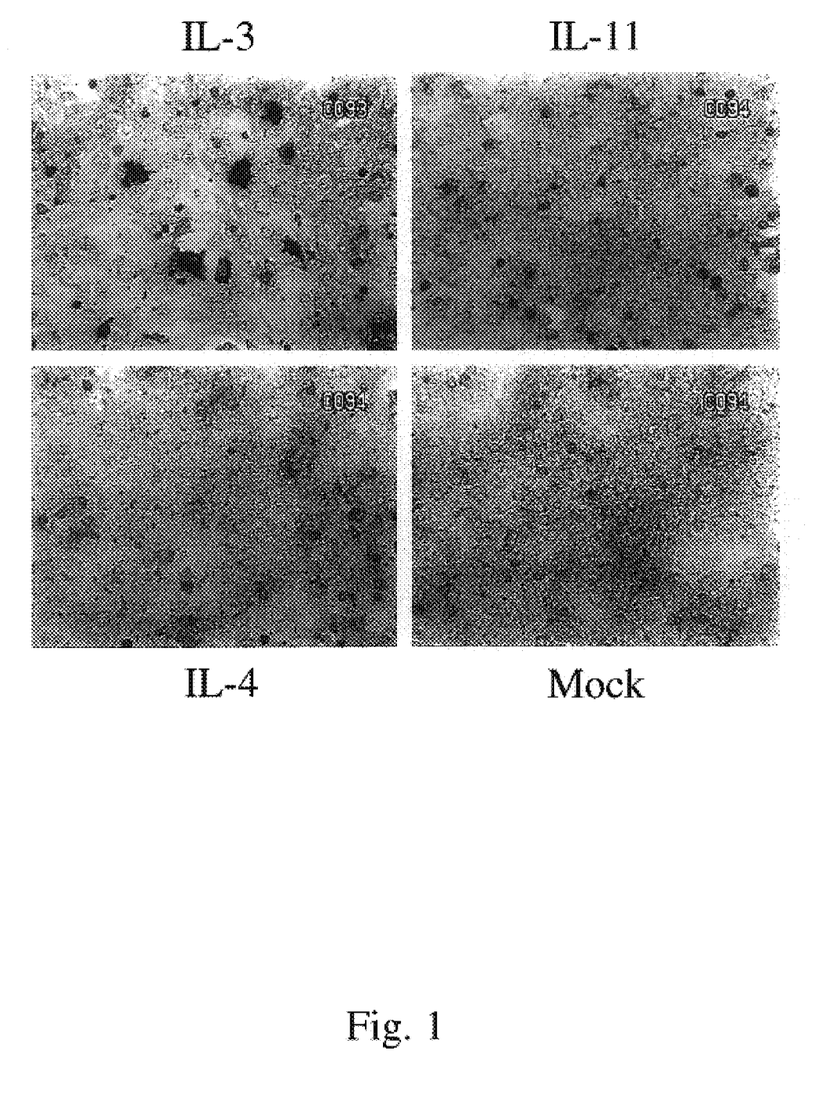

Specific binding was visualized under the microscope. Only cells transfected with IL-13 showed specific binding to IL-13bc-Ig. (see photo of transfected cells, the FIGURE).

EXAMPLE 5

Other Systems for Determination Biological Activity of IL-13bc Protein

Other systems can be used to determine whether a specific IL-13bc protein exhibits a "biological activity" of IL-13bc as defined herein. The following are examples of such systems.

Assays for IL-13 Binding

The ability of a IL-13bc protein to bind IL-13 or a fragment thereof can be determined by any suitable assays which can detect such binding. Some suitable examples follow.

Binding of IL-13 to the extracellular region of the IL-13bc protein will specifically cause a rapid induction of phosphotyrosine on the receptor protein. Assays for ligand binding activity as measured by induction of phosphorylation are described below.

Alternatively, a IL-13bc protein (such as, for example, a soluble form of the extracellular domain) is produced and used to detect IL-13 binding. For example, a DNA construct is prepared in which the extracellular domain (truncated prior, preferably immediately prior, to the predicted transmembrane domain) is ligated in frame to a cDNA encoding the hinge $C_H2$ and $C_H3$ domains of a human immunoglobulin (Ig) γ1. This construct is generated in an appropriate expression vector for COS cells, such as pEDΔC or pMT2. The plasmid is transiently transfected into COS cells. The secreted IL-13bc-Ig fusion protein is collected in the conditioned medium and purified by protein A chromatography.

The purified IL-13bc-Ig fusion protein is used to demonstrate IL-13 binding in a number of applications. IL-13 can be coated onto the surface of an enzyme-linked immunosorbent assay (ELISA) plate, and then additional binding sites blocked with bovine serum albumin or casein using standard ELISA buffers. The IL-13bc-Ig fusion protein is then bound to the solid-phase IL-13, and binding is detected with a secondary goat anti-human Ig conjugated to horseradish peroxidase. The activity of specifically bound enzyme can be measured with a colorimetric substrate, such as tetramethyl benzidine and absorbance readings.

IL-13 may also be expressed on the surface of cells, for example by providing a transmembrane domain or glucosyl phosphatidyl inositol (GPI) linkage. Cells expressing the membrane bound IL-13 can be identified using the IL-13bc-Ig fusion protein. The soluble IL-13bc-Ig fusion is bound to the surface of these cells and detected with goat anti-human Ig conjugated to a fluorochrome, such as fluorescein isothiocyanate and flow cytometry.

Interaction Trap

A yeast genetic selection method, the "interaction trap" [Gyuris et al., Cell 75:791-803, 1993], can be used to determine whether a IL-13bc protein has a biological activity of IL-13bc as defined herein. In this system, the expression of reporter genes from both LexAop-Leu2 and LexAop-LacZ relies on the interaction between the bait protein, for example in this case a species which interacts with human IL-13bc, and the prey, for example in this case the human IL-13bc protein. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

In such methods, if one wishes to determine whether the IL-13bc protein interacts with a particular species (such as, for example, a cytosolic protein which binds to the intracellular domain of the IL-13bc in vivo), that species can be used as the "bait" in the interaction trap with the IL-13bc protein to be tested serving as the "prey", or vice versa.

All patent and literature references cited herein are incorporated by reference as if fully set forth.

What is claimed is:

1. A method of inhibiting binding of IL-13 an IL-13 binding chain (IL-13bc) in a mammalian subject, the method comprising administering to the mammalian subject an effective amount of a composition comprising an antibody that specifically binds to the IL-13bc, said IL-13bc comprising an amino acid sequence selected from the group consisting of:
   the amino acid sequence of SEQ ID NO: 4:
   the amino acid sequence of SEQ ID NO: 4 from amino acids 26 to 341; and
   the amino acid sequence of SEQ ID NO: 4 from amino acids 26 to 380,
thereby inhibiting binding of IL-13 to the IL-13bc.

2. A method of inhibiting binding of IL-13 to an IL-13 receptor or an IL-13 binding chain (IL-13bc) in a mammalian subject, the method comprising administering to the mammalian subject an effective amount of a composition comprising an antibody that inhibits binding of IL-13 to the IL-13bc or the IL-13 receptor, said IL-13bc comprising an amino acid sequence selected from the group consisting of:
   the amino acid sequence of SEQ ID NO: 4;
   the amino acid sequence of SEQ ID NO: 4 from amino acids 26 to 341; and
   the amino acid sequence of SEQ ID NO: 4 from amino acids 26 to 380
thereby inhibiting binding of IL-13 to the IL-13 receptor or IL-13bc.

3. The method of claim 1, wherein the mammalian subject is a human.

4. The method of claim 1, wherein the antibody is a monoclonal or a polyclonal antibody.

5. The method of claim 1, wherein the antibody is a neutralizing antibody.

6. A method of inhibiting a biological activity of IL-13 in a mammalian subject, the method comprising administering to the mammalian subject an effective amount of a composition comprising an antibody that specifically binds to an IL-13 binding chain (IL-13bc), said IL-13bc comprising an amino acid sequence selected from the group consisting of:
   the amino acid sequence of SEQ ID NO: 4;
   the amino acid sequence of SEQ ID NO: 4 from amino acids 26 to 341; and
   the amino acid sequence of SEQ ID NO: 4 from amino acids 26 to 380,
thereby inhibiting the biological activity of IL-13, wherein the biological activity is selected from the group consisting of induction of IgG4 and IgE switching, induction of germ line IgE heavy chain transcription and CD23 expression, and induction of B cell proliferation in the presence of CD40L or anti-CD40 monoclonal antibody.

7. The method of claim 6, wherein the mammalian subject is a human.

8. The method of claim 6, wherein the biological activity of IL-13 comprises binding to the IL-13bc.

9. The method of claim 6, wherein the antibody is a monoclonal or a polyclonal antibody.

10. The method of claim 6, wherein the antibody is a neutralizing antibody.

11. The method of claim 1 or 2, wherein the composition further comprises a pharmaceutically acceptable carrier.

12. The method of claim 2, wherein the mammalian subject is a human.

13. The method of claim 2, wherein the biological activity of IL-13 comprises binding to the IL-13bc.

14. The method of claim 2, wherein the antibody is a monoclonal or a polyclonal antibody.

15. The method of claim 2, wherein the antibody is a neutralizing antibody.

16. A method of inhibiting binding of IL-13 to an IL-13 binding chain (IL-13bc) in a mammalian subject, the method comprising administering to the mammalian subject a composition comprising an antibody to a fragment of IL-13bc in an amount effective to inhibit binding of IL-13 to the fragment of the IL-13bc, wherein said fragment of IL-13bc comprises amino acids 26-341 of SEQ ID NO:4 or 26-380 of SEQ ID NO:4 and binds to IL-13 with a $K_D$ of from 0.1 to 100 nM.

17. The method of claim 16, wherein the mammalian subject is a human.

18. The method of claim 16, wherein the antibody is a monoclonal or a polyclonal antibody.

19. The method of claim 16, wherein the antibody is a neutralizing antibody.

20. A method of inhibiting binding of IL-13 to an IL-13 binding chain (IL-13bc) in a mammalian subject, the method comprising administering to the mammalian subject an effective amount of a composition comprising an antibody to an IL-13bc variant protein encoded by a nucleic acid sequence that hybridizes to the complement of the nucleotide sequence set forth in SEQ ID NO:3 under hybridization conditions of 0.1×SSC at 65° C. followed by wash conditions of 2×SSC at 52° C., wherein the nucleic acid sequence encodes a protein that binds to IL-13.

21. The method of claim 20, wherein the mammalian subject is a human.

22. The method of claim 20, wherein the antibody is a monoclonal or a polyclonal antibody.

23. The method of claim 20, wherein the antibody is a neutralizing antibody.

24. A method of inhibiting binding of IL-13 to an IL-13 binding chain (IL-13bc) in a mammalian subject, the method comprising administering to the mammalian subject an effective amount of a composition comprising an antibody to an IL-13bc variant protein that is at least about 95% identical to a protein selected from the group consisting of the amino acid sequence of SEQ ID NO:4; and the amino acid sequence of SEQ ID NO:4 from amino acids 26 to 341; wherein the IL-13bc variant protein binds to IL-13.

25. The method of claim 24, wherein the mammalian subject is a human.

26. The method of claim 24, wherein the antibody is a monoclonal or a polyclonal antibody.

27. The method of claim 24, wherein the antibody is a neutralizing antibody.

28. A method of inhibiting a biological activity of IL-13 in a mammalian subject, the method comprising administering to the mammalian subject an effective amount of an antibody that inhibits binding of IL-13 to an IL-13 binding chain (IL-13bc) or an IL-13 receptor, said IL-13bc comprising an amino acid sequence selected from the group consisting of:

the amino acid sequence of SEQ ID NO: 4;

the amino acid sequence of SEQ ID NO: 4 from amino acids 26 to 341;

the amino acid sequence of SEQ ID NO: 4 from amino acids 26 to 380, wherein the biological activity is selected from the group consisting of induction of IgG4 and IgE switching, induction of germ line IgE heavy chain transcription and CD23 expression, and induction of B cell proliferation in the presence of CD40L or anti-CD40 monoclonal antibody.

29. The method of claim 28, wherein the mammalian subject is a human.

30. The method of claim 28, wherein the antibody is a monoclonal or a polyclonal antibody.

31. The method of claim 28, wherein the antibody is a neutralizing antibody.

* * * * *